United States Patent [19]
Kinnunen et al.

[11] Patent Number: 5,879,950
[45] Date of Patent: Mar. 9, 1999

[54] MATERIALS AND METHODS FOR DIGESTION OF DNA OR RNA USING RESTRICTION ENDONUCLEASES

[76] Inventors: Paavo Kai Johannes Kinnunen, Punarinnantie 4, FIN-02660 Espoo; Pekka Kristian Mustonen, Nuolitie 36, FIN-02240 Espoo; Juha Kalervo Kere, Kuusmiehentie 36 J, FIN-00670 Helsinki, all of Finland

[21] Appl. No.: 484,769

[22] Filed: Jun. 7, 1995

Related U.S. Application Data

[63] Continuation-in-part of Ser. No. 264,080, Jun. 22, 1994, abandoned.
[51] Int. Cl.$^6$ .............................. G01N 1/00; G01N 1/18; C07C 1/02; C07D 1/02
[52] U.S. Cl. .................... 436/175; 436/176; 436/177; 436/178; 435/262; 435/264; 435/68.1; 435/69.1; 435/69.2; 435/41; 435/182; 435/183; 435/195; 435/814; 435/173.4; 205/777.5
[58] Field of Search .................. 435/91.1, 91.2, 435/91.52, 91.53, 199, 173.4, 6, 41, 68.1, 69.1, 69.2, 262, 264, 814, 183, 195, 182; 935/23; 536/23.1, 22.1, 124; 204/182.8; 205/777.5; 436/175, 176, 177, 178

[56] References Cited

PUBLICATIONS

New England Biolabs Catalog, p. 196, 1995.
Batzri et al. "Single bilayer liposomes prepared without sonication". Biochemica et Biophysica Acta., vol. 298, pp. 1015–1019, 1973.
Heitman, "On the Origins, Structures and Functions of Restriction–Modification Enzymes," *Genetic Engineering*, 15:57–108, Plenum Press, New York (1993).
Heitman, "SOS induction as an in vivo assay of enzyme – DNA interactions," *Gene*, 103:1–9 (1991).
Kere, et al., "Mapping Human Chromosomes by Walking with Sequence–Tagged Sites from End Fragments of Yeast Artificial Chromosome Inserts," *Genomics*, 14:241–248 (1992).
Budker, et al., *Chemical Abstracts*, 116:152013b (1987).
Mixich, "Induction of chromosomal aberrations by restriction endonucleases encapsulated in liposomes," *Mutation Research*, 262:177–181 (1991).
Bryant, et al., "Induction of chromosomal aberrations in CHO cells by restriction endonucleases: effects of blunt–and cohesive–ended double–strand breaks in cells treated by 'pellet' methods," *Mutation Research*, 213:233–241 (1989).
Obe, et al., "Chromosomal aberrations induced by restriction endonucleases," *Mutation Research*, 150:359–368 (1985).

*Primary Examiner*—Kenneth R. Horlick
*Assistant Examiner*—Datquan Lee
*Attorney, Agent, or Firm*—Marshall, O'Toole, Gerstein, Murray & Borun

[57] ABSTRACT

Disclosed are improvements for enzyme-catalyzed reactions involving DNA or RNA, including restriction digests, which are based on conducting such reactions in the presence of lipids.

35 Claims, 5 Drawing Sheets

MATERIALS AND METHODS FOR DIGESTION OF DNA OR RNA USING RESTRICTION ENDONUCLEASES

This application is a continuation-in-part of U.S. patent application, Ser. No. 08/264,080, filed Jun. 22, 1994, now abandoned.

FIELD OF THE INVENTION

The present invention generally relates to materials and methods for the controlled modification of DNA- or RNA-enzyme interactions by coupling such reactions to lipids.

BACKGROUND OF THE INVENTION

Enzymes which act upon DNA or RNA, such as restriction endonucleases and exonucleases, ligases, polymerases, and others, have become widely available for use in research applications requiring modification, copying, and/or activation (e.g., transcription) of DNA. For example, restriction digests of DNA using specific endonucleases has aided in the recombinant expression of genes, and has been used for mapping and for cloning and sequencing DNA, as well as for the construction of specific probes for research and diagnostic applications.

Of interest to the present invention are numerous methods involving DNA or RNA modification which are improved upon by the invention. In the present application, methods for DNA or RNA modification include any method in which an enzyme, together with possible auxiliary proteins, acts upon DNA or RNA.

One of the most common methods involving DNA modification involves the digestion of DNA using restriction endonucleases. The most common restriction endonucleases cleave DNA at specific recognition sites within the DNA sequence. Sites at which a DNA sequence is interrupted (cleavage sites) are usually 4–8 base pairs long. Restriction digests are useful for the ultimate production of probes and for incorporation of fragments produced thereby into a vector for expression of a gene product or for cloning purposes. Especially where large amounts of DNA are to be digested, restriction digests may require large amounts of enzyme which are expensive and considerable time may be required for the reaction to run to completion.

Reactions involving DNA modification, such as those described above, are conventionally carried out in aqueous solution in the presence of organic and inorganic salts, buffers, and the required enzymes. The reaction mixtures must be incubated at optimized temperatures for set periods of time in order for the reaction to run to completion.

Also of interest to the present invention are lipids and their physical chemical properties. Lipids exhibit characteristic phase behavior which is a function of, inter alia, temperature and ionic concentrations. Lipid phase transitions are accompanied by dramatic alterations in physical organization. It is now established that several proteins bind to lipids in biological membranes and that such binding is a function of the phase state of the membrane lipids. By changing the physical state of the lipids in the bilayer, one may cooperatively regulate the binding, and therefore, the function of proteins which bind to the lipids. Specifically, several DNA-binding proteins have been shown to bind to lipids, with resulting changes in function depending upon the lipid phase state.

Phospholipids, for example, which are found in all cellular membranes, comprise two very different physical environments, a hydrophobic interior region and a more-complex hydrophilic exterior region. The hydrophobic tails of most phospholipids exist in two fundamental physical states. At higher temperatures the hydrophobic tails are in a fluid state and generally have rotational freedom; while at lower temperatures, phospholipids are more geometrically constrained. Overall, membrane lipids may exist in varying states of order, or phases, which normally depend upon both temperature and the lipid composition. There are four major forms of organization of lipids in a biological environment (i.e., in the presence of water). The lamellar liquid crystalline phase ($L_\alpha$) is the fluid state normally depicted in representations of biological membranes. The lamellar gel phase ($L_\beta$) is formed at low temperatures in lipids in which the lamellar structure is possible. The $L_\beta$ phase is characterized by tight packing and acyl chains which are more highly ordered as compared to the $L_\alpha$ phase. The $L_\beta$ phase is also characterized by a predominance of the all-trans acyl chain configuration, resulting in greater bilayer thickness than in the $L_\alpha$ phase. In the Hexagonal I phase ($H_I$), lipids are organized in cylinder-like configurations, with the polar head groups facing outward. Finally, the Hexagonal II phase ($H_{II}$) is characterized by a hexagonal array of cylinders, but with the polar head groups facing inward, surrounding a column of water (i.e., an inverted micelle). The phase adopted by a particular lipid is a function of, inter alia, temperature and the precise mix of lipids present. For example, some lipids, such as unsaturated phospatidylethanolamines, resist bilayer formation and tend toward the $H_{II}$ configuration. However, the overall configuration of a biological membrane is determined by the sum of phospholipids present, taking into account other factors, such as temperature, ionic strength, and hydration. The kinetic properties of membranes are due, in large part, to the properties of the phospholipids which comprise them. Membrane lipids create a fluid environment in which conformational changes in both membrane proteins and the lipids themselves allow a diversity of reactions to take place at the membrane which cause changes in cellular processes, including growth. The extent of fluidity in the membrane is a function of temperature, as indicated above, and also of the ratio of phospholipid to cholesterol and the extent of saturation of membrane lipids. One of the more important roles of membrane phospholipids occurs in the regulation of binding between membrane-bound receptors and their ligands.

The present invention provides materials and methods for enhancing the yield of restriction digestions, including enhancements in the amount of digestion production obtained per unit time, enhancements in the speed of digestion, enhancements in specificity, and reduced requirements for enzyme.

SUMMARY OF THE INVENTION

The present invention relates to methods and materials for enhancement of reactions involving RNA or DNA modification by conducting such reactions in the presence of lipids.

In a preferred embodiment of the invention, a DNA is digested using one or more restriction endonucleases in the presence of a lipid in the form of a liposome or a micelle. The digestion is carried out in a reaction buffer specified by the manufacturer of the restriction endonuclease or in a potassium glutamate buffer. Buffers for use in methods of the invention are reported, for example, in the New England Biolabs Catalog, 196 (1995). Such improved methods according to the invention result in much more rapid and complete digestion of DNA and decreased catalyst requirements, resulting in decreased costs.

Preferred lipids for use in the present invention comprise a phosphorylcholine moiety attached to a hydrophobic tail. Highly preferred embodiments of the invention include didecyl phosphatidylcholine in an effective concentration ranging from about 10 $\mu$M to about 50 $\mu$M.

In a preferred embodiment of the invention, a DNA plasmid comprising a heterologous gene for expression is constructed in the presence of a lipid; wherein such construction, including digestion of DNA containing said heterologous gene and ligation of said heterologous gene in said plasmid occurs at a much more rapid rate than is reported in the art.

Also in a preferred embodiment of the invention, in vitro transcription rates are increased, wherein a gene in an expression vector is expressed in the presence of enzymes necessary for expression in the presence of lipids. Such procedures increase transcription rates as well as the fidelity of the resulting transcript.

The present invention is also useful in the improvement of the kinetics, specificity, and yield of enzyme-catalyzed reactions. Thus, in a preferred embodiment of the invention, enzymatic reactions catalyzed by nucleotide kinases and/or phosphatases are improved by conducting such reactions in the presence of a lipid.

Upon consideration of the present invention, the skilled artisan understands that the invention may be applied to any method in which RNA or DNA is acted upon by enzymes. Based upon the principles of the invention, it is understood that conducting such reactions in the presence of a lipid increases the speed and specificity of such reactions and reduces the requirements for enzyme and other materials, resulting in a considerable cost savings. Accordingly, numerous applications of the invention, in addition to those exemplified herein, are readily apparent to the skilled artisan upon consideration of the present application.

DETAILED DESCRIPTION OF THE INVENTION

Standard reaction conditions in various enzyme-catalyzed reactions, and especially reactions involving DNA, are generally suboptimal, resulting in poor yields and reduced specificity.

In a general sense, the present invention improves conventional techniques by tying reactions involved in those techniques to a lipid. Such improvements may be mediated through lipid-protein or lipid-DNA interactions, possibly reducing activation energies; altered dimensionality of the reactions; and other effects, either alone or in combination. Whatever the mechanism, conducting such reactions in the presence of lipids results in enhanced reaction rates, shorter incubation times, improved yields, and altered reaction temperatures.

Lipids for use in the invention are preferably of the formula X—PO$_4^-$—Y, wherein X is a phosphorylcholine moiety and Y is a hydrophobic moiety. Examples of such lipids include didecyl phosphatidylcholine, egg yolk phosphatidylcholine, dimyristoyl phosphatidylcholine, sphingomyelin, sphingosyl phosphatidylcholine, and 1-palmitoyl-2-octyl phosphatidylcholine. Both micelle-forming lipids, such as 1-palmitoyl-2-acetyl phosphatidylcholine, and liposome-forming lipids, such as didecyl phosphatidylcholine, may be used according to the invention.

Improvements in restriction digestion according to the invention are measured as an apparent increase in enzyme activity resulting from the addition of lipids. An apparent increase in enzyme activity represents the dilution of enzyme which may be used in the presence of lipids to achieve digestion (either complete or partial) in a specified incubation time equivalent to that achieved with undiluted enzyme. For example, an apparent increase in enzyme activity of 243× means that a 243-fold dilution of enzyme in the presence of lipid provides digestion of a given polynucleotide substrate which is equivalent to that produced by undiluted enzyme in the same time period.

Methods of the invention have been carried out with numerous different lipids. Lipids producing the greatest enhancement of restriction endonuclease activity possess a phosphorylcholine moiety linked to a hydrophobic chain. Examples of such lipids include, but are not limited to, 1-palmitoyl-2-acetyl phosphatidylcholine, didecyl phosphatidylcholine, and phosphatidylcholine derived from egg yolk.

Numerous different restriction enzymes have been enhanced by methods of the invention as described below. In fact, presently-claimed methods have enhanced digestion with every endonuclease tested. Digestion is considered to be enhanced if digestion obtained with dilute quantities of enzyme in the presence of lipids that is roughly equivalent to digestion obtained using undiluted enzyme. Digestion is also considered to be enhanced if digestion in the presence of lipids is more rapid than digestion without lipids using equivalent amounts of enzyme and digestion time. The overall enhancement of restriction digestion will become apparent upon consideration of the preferred embodiments for practicing the invention.

Experiments were conducted to determine the effect of lipid addition on the digestion of bacteriophage lambda DNA using various lipids in combination with restriction endonucleases. The lipids were added to the reaction buffer specified for each endonuclease by the manufacturer. Lipids were added to the reaction mixture as micelles or liposomes, depending upon the lipid composition. For example, certain lipids, such as sphingosyl phosphatidylcholine, 1-palmitoyl-2-octyl phosphatidylcholine, and lyso phosphatidylcholine, spontaneously form micelles in polar solution. Thus, such lipids may be dissolved in ethanol and injected into the reaction buffer or they may be prepared as a dry lipid film to which buffer is added. Other lipids are prepared for use in the invention as either multilamellar or unilamellar liposomes as described below. Experiments demonstrated that the enhancing effect on restriction digestion did not depend upon whether lipids formed micelles or liposomes.

EXAMPLE 1

Enhancement of Partial Restriction Digests Using Lipids

In order to determine the extent to which lipids enhance restriction endonuclease digestion, bacteriophage lambda DNA was digested using various restriction enzymes in the presence of lipids. Serial dilutions of enzyme were made and restriction digests were carried out in the presence of egg yolk phosphatidylcholine and stearylamine. In this experiment, overall enhancement was determined by measurement of the lowest enzyme concentration which produced any digestion on an agarose gel in the presence of lipid as compared to the lowest enzyme concentration which produced any digestion without lipid addition. For example, a 32-fold apparent increase in activity is determined by injection of an agarose gel showing that lipid addition enabled the enzyme to produce at least partial digestion at a 32-fold dilution.

Accordingly, repeated experiments were performed to determine the effect of various lipids on the activity and kinetics of restriction endonucleases. Lipid preparations were made by rapidly injecting ethanol solutions of lipids into the appropriate buffer (see below), yielding liposome suspensions of between 100 $\mu$M to 500 $\mu$M, as reported in Batzri, et al., *Biochem. Biophys. Acta*, 298: 1015–1019 (1973), incorporated by reference herein. The suspensions were stored at 4° C. for several weeks without loss of activity and were then further diluted with reaction buffer prior to each run. Restriction digests were incubated in buffers as recommended by the manufacturer of each enzyme, as shown in Table 1 below.

TABLE 1

| ENZYME | MANUFACTURER | BUFFER | APPARENT INCREASE IN ENZYME ACTIVITY |
| --- | --- | --- | --- |
| AluI | Promega; NEB | B(Promega) 1(NEB) | 32 fold |
| BamHI | NEB | BamHI | none |
| BGIII | Promega | D | 2- to 4-fold |
| EcoRV | NEB | 2 | 2- to 4-fold* |
| HaeIII | Promega | C | 2-fold |
| HindIII | Promega | HindIII | 2- to 4-fold** |
| PstI | NEB | 3 | none |
| PvuII | Promega | B | 4- to-8-fold* |
| RsaI | NEB | 1 | 8- to 16-fold |
| StuI | Promega | B | 16-fold |
| TaqI | NEB | TaqI | 32-fold |

*(egg yolk phosphatidylcholine (EPC) > EPC:STA **EPC:STA > EPC

Figure 1A:
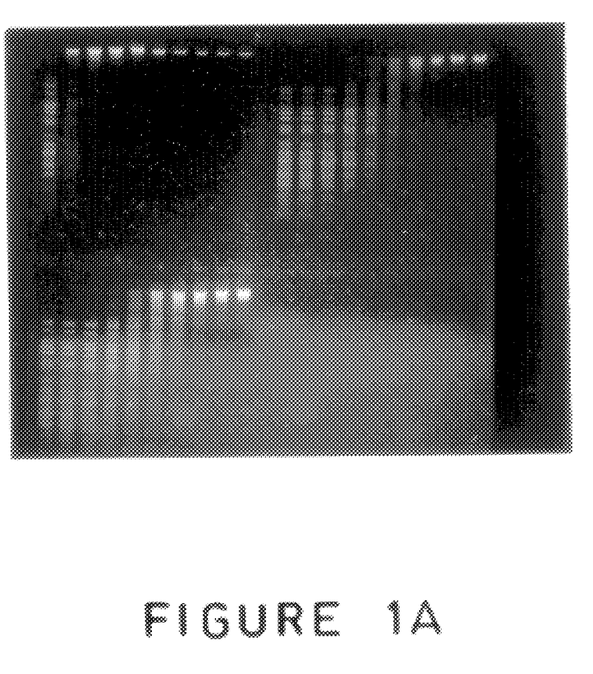
FIG. 1A shows 1% Agarose gels stained with ethidium bromide which provide results of digestion of bacteriophage lambda DNA with AluI.
Figure 1B:
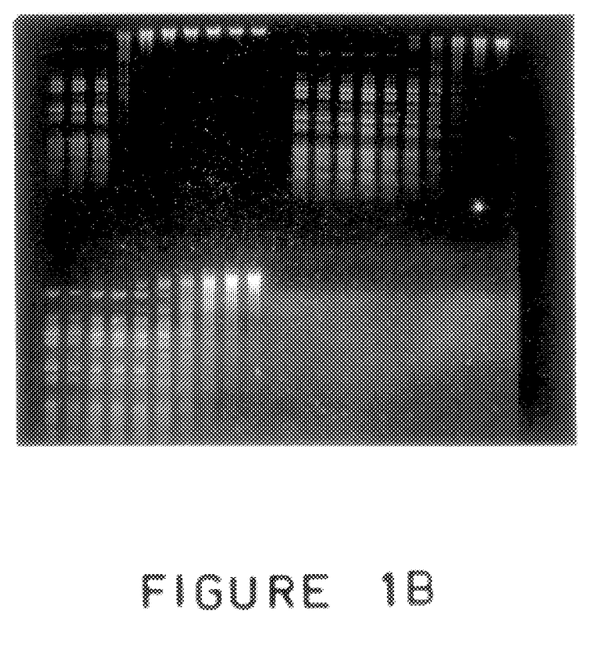
FIG. 1B shows 1% Agarose gels stained with ethidium bromide which provide results of digestion of bacteriophage lambda DNA with TaqI.

For evaluation of each endonuclease included in Table 1, the assay conditions were as follows: 1 $\mu$g of bacteriophage lambda DNA was incubated in 25 $\mu$l reaction volumes for 1 hour at 37° C. (65° C. for TaqI), using the appropriate buffer with the indicated enzyme. A series of ten two-fold dilutions of each enzyme was tested (10, 5, 2.5, 1.3, 0.63, 0.31, 0.164, 0.078, 0.039, 0.02 U). The enzyme dilutions were aliquoted in three parallel sets of reactions, one with no lipid, another with 10 $\mu$M EPC:STA in a molar ratio of 1:1, and the third with 10 $\mu$M EPC. Reaction time varied between about 5 minutes and about 4 hours at 37° C. Control runs included duplicate reaction tubes at identical concentrations of reagents but with no lipid. Eleven different restriction enzymes were tested. The restriction digests were stopped by the addition of 3 $\mu$l xylene cyanol-bromophenol blue loading buffer with 5% sodium dodecyl sulphate, and either loaded immediately to gels or stored frozen until electrophoresed. The extent of digestion was estimated visually from 1% agarose gels stained with ethidium bromide. Overall results are shown in Table 1 and typical results are shown in FIGS. 1A and 1B which represent increases in apparent enzyme activity of AluI and TaqI, respectively, with the addition of EPC or EPC:STA in a 1:1 molar ratio versus activity with no lipid added. In FIGS. 1A and 1B, the upper left quadrant shows result obtained when no lipid was added; the upper right quadrant shows results obtained when EPC:STA was added; and the lower left quadrant shows results obtained when 10 $\mu$M EPC was added to the reaction mixture. The lower right quadrant is blank in FIGS. 1A and 1B. In each of those Figures, lanes 1–10 represent from 10 to 0.02 U of enzyme as indicated above. From the data above, it was determined that 10 $\mu$M EPC provided the greatest increase in enzyme activity in the assay described above.

For the restriction endonuclease, RsaI, lipid concentrations of between about 250 $\mu$M and about 2 $\mu$M increased the activity of the enzyme. That effect increased with increasing lipid concentrations but decreased again at concentrations higher than 25 $\mu$M. The optimal lipid concentration for RsaI was 10 $\mu$M, at which concentration a 16-fold smaller amount of the enzyme was necessary to cause digestion in a 30 minute reaction in comparison to the same reaction run without lipid. For TaqI, using a digestion at 65° C., the enhancement of activity was 32-fold (i.e., 32-fold less enzyme was necessary to digest a target DNA as compared to reactions run without lipid).

Figure 2:
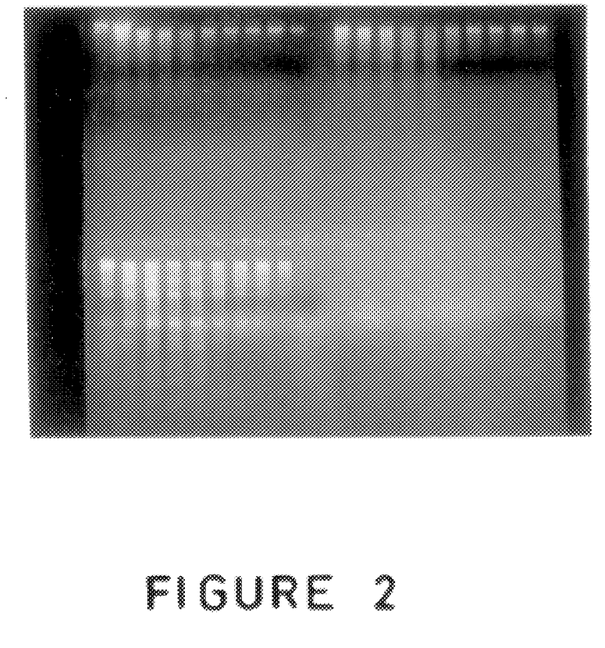
FIG. 2 depicts optimum concentrations of lipids for use in increasing the activity of RsaI.

Using RsaI, significant digestion was evident 10 minutes after the start of the reaction when lipid was present in the reaction mixture. A similar amount of digestion as that observed after 10 minutes of exposure to RsaI in lipid was not observed in the control even after two hours of digestion. Of the 11 endonucleases tested, AluI, EcoRV, HaeIII, HindIII, PvuII, RsaI, StuI, BglII, and TaqI were found to have an increase in activity from 4- to 32-fold when lipids were present (See TABLE 1). Agarose gel electrophoresis showed that the restriction pattern was the same in all experiments for each endonuclease, suggesting that the lipids did not change the specificity of the enzymes. Interestingly, EPC (phosphatidylcholine from egg yolk) alone increased the activity of RsaI and AluI at least as effectively as the 1:1 mixture of EPC:STA; whereas for HindIII, the EPC:STA mixture enhanced enzyme activity more than EPC alone. That result suggests that by varying the lipid molecules used and their molar ratios, it is possible to control the apparent activity of many, if not all, restriction endonucleases. Results of RsaI (1 U) digests in the presence of EPC:STA, showing optimal concentrations are provided in FIG. 2. In that Figure, the concentrations (expressed in $\mu$M) of lipid used are, from left to right, 100, 50, 25, 13, 6.3, 3.1, 1.6, 0.78, 0.39, and none. The upper left quadrant is a gel obtained after 5 minutes (i.e., the reaction was stopped at 5 minutes); the upper right quadrant is a gel obtained after 15 minutes; and the lower left quadrant is a gel obtained after 45 minutes. The lower right quadrant is blank in FIG. 2. The most advanced digestion was observed at lipid concentration of 13 $\mu$M and 6.3 $\mu$M (lanes 4 and 5).

The foregoing results show that the addition of lipids to reaction mixtures in which DNA-modifying enzymes are involved provides greatly enhanced yields, decreased reaction times, and lower requirements for starting materials. As such, presently-claimed methods provide a significant advance in the art of DNA manipulation and provide significant improvements in standard techniques, such as restriction digests. Numerous additional embodiments of the invention are apparent to the skilled artisan upon consideration of the foregoing description thereof. Accordingly, the foregoing description is to be considered exemplary and not as a limitation on the scope of the invention which is claimed as follows.

EXAMPLE 2

Enhancement of Complete Restriction Digestion Using Lipids

A second set of experiments was designed to measure the extent to which lipid addition enhances complete restriction endonuclease digestion. By definition, one unit of a restriction endonuclease is the amount necessary to completely digest 1 μg of substrate DNA in a reaction volume of 50 μl in one hour. Thus, a measure of the enhancement of restriction digestion achieved in the presence of lipids in the dilution of enzyme which may be used to achieve complete digestion in one hour when lipids are present in the reaction buffer.

Lipid preparations were made as described above using either 10 μM egg phosphatidylcholine or 25 μM didecyl phosphatidylcholine. Digestion was performed in a suitable reaction buffer recommended by the manufacturer of the enzyme. In each case, 1 μg of bacteriophage lambda DNA was reacted in a 50 μl reaction volume for 1 hour at 37° C. (65° C. for TaqI). A series of ten two-fold dilutions was carried out for each enzyme in the presence of either egg phosphatidylcholine or didecyl phosphatidylcholine. A control reaction was also carried out wherein no lipid was added to the reaction mixture. the results provided below in Table 2 reflect the dilution of enzyme which could be used to achieve complete digestion under the foregoing reaction conditions.

The results for 13 representative restriction enzymes are presented below in Table 2, where results are provided in terms of the apparent increase in enzyme activity achieved in the presence of lipid.

TABLE 2

| Enzyme | 10 μM eggPC | 25 μM DDPC |
|---|---|---|
| StuI | 2–4x | 4–16x |
| AluI | 1x | 2–4x |
| EcoRv | 2x | 16–32x |
| BamHI | 1x | 4–8x |
| PuII | 4x | 16x |
| TaqI | 1x | 4x |
| RsaI | 1x | 2x |
| BglII | 1x | 2x |
| HaeIII | 2x | 2x |
| HindIII | 2x | 4–8x |
| pstI | 1x | 2–4x |
| BasII | — | 16x |
| BglI | — | 4x |

In the above experiments, egg yolk phosphatidylcholine ("eggPC") was prepared as a 1:1 mixture of 10 μM eggPC and stearylamine. The results show relatively moderate increases in activity with egg PC and rather large increases with didecyl phosphatidylcholine (DDPC). For example, StuI may be diluted up to 16-fold and still produce complete digestion of bacteriophage lambda DNA in one hour.

The effective concentration of didecyl phosphatidylcholine in a one hour HindIII digest was between 10 μM and 125 μM.

In a separate experiment, the activation of various endonucleases was determined in the presence of potassium glutamate buffer as a universal buffer (100 mM potassium glutamate, 10 mM Mg-acetate, 25 mM Tris acetate, 0.5 mM mercaptoethanol, pH 7.6) and 25 μM didecyl phosphatidylcholine. The reaction mixtures were prepared as above and allowed to proceed for one hour. As shown below, activation takes place which, in some cases, is better that achieved using the buffer specified by the enzyme manufacturers.

TABLE 3

| Enzyme | Apparent increase in activity |
|---|---|
| StuI | 4x |
| AluI | 2x |
| EcoRI | 2x |
| BamHI | 4–8x |
| PuII | 2x |
| TaqI | 4–8x |
| RsaI | 2x |
| BglI | 1–2x |
| HaeII | 2x |
| HindIII | 4–8x |
| BglII | 2x |
| Sau3AI | 2x |

As shown in this Table, potassium glutamate buffer is useful as a universal buffer for activation of restriction endonucleases in methods of the invention.

EXAMPLE 3

Effect of Glycerophospholipids in Restriction Endonuclease Activation

An experiment was conducted to determine the effect of glycerophospholipids generally on the activation of two restriction endonucleases. The experimental conditions were identical to those described above. Lipids were added to the reaction mixture at a concentration of 25 μM and the reaction was allowed to take place for one hour. The results are shown below in Table 4.

TABLE 4

| LIPID | HindIII | RsaI |
|---|---|---|
| Didecyl-PC | 4 x | 2–4 x |
| Didecanoyl-PC | 4 x | 2–4 x |
| Dimyristoyl-PC | 8–16 x | 2 x |
| Dihexadecyl-PC | 4–8 x | 2 x |
| Dipalmitoyl-PC | 4–8 x | 2 x |
| Dioleoyl-PC | 4–8 x | 2 x |
| EggPC | 4–8 x | 2–4 x |
| Dimyristoyl-PC - Sta 1:1 | 16–32 x | |
| EggPC - Sta 1:1 | 16–32 x | |

As shown in Table 4 above, glycerophospholipids generally provide activation of restriction enzymes, with the highest activation seen on HindIII incubated with egg phosphatidylcholine-stearylamine or dimyristoyl phosphatidylcholine-stearylamine.

EXAMPLE 4

Effect of Phosphorylcholine-Containing Lipids on Restriction Endonuclease Activation Further experimental evidence indicated that lipids having a phosphorylcholine moiety provided the highest degree of activation. To test that hypothesis, non-phosphorylcholine-bearing lipids were tested under conditions identical to those reported above. Each of the lipids in Table 5 below was added to the manufacturer's restriction buffer which contained StuI in varying concentrations. The reaction was allowed to occur for one hour. Results shown in Table 5, indicate that lipids not bearing the phosphorylcholine moiety do not provide activation of StuI and may, in certain cases, hinder activity.

TABLE 5

| LIPID | StuI Activity |
|---|---|
| Dimyristoyl phosphatidylglycerol (DMPG) | 1 x |
| Dimyristoyl phosphatidylserine (DMPS) | −4 x |
| Dimyristoyl phosphatidyl ethanolamine and DMPG 1:1 | −4 x |
| DMPS and Egg phosphatidylcholine 1:1 | −4 x |
| DMPG and Egg phosphatidylcholine 1:3 | 1 x |
| Bovine phosphatidylinositol | 1 x |
| Egg phosphatidic acid | 1 x |
| Palmitic acid | 1 x |

An additional experiment was conducted to determine activation of StuI in the presence of phosphorylcholine-containing lipids. Reaction conditions were the same as those described above. The reactions were allowed to take place for either one hour or one day. Reactions were conducted using three liposome-forming lipids and three micelle-forming lipids. Results are provided below in Table 6.

TABLE 6

| Liposome-forming lipids | Micelle-forming lipids | 1 hour | 1 day |
|---|---|---|---|
| Egg yolk phosphatidylcholine | | 2x | 16x |
| Didecyl phosphatidylcholine | | 9x | 81x |
| Sphingomyelin | | 3x | 27x |
| | Sphingosyl phosphatidylcholine | 9x | 243x |
| | 1-palmitoyl-2-octyl- phosphatidylcholine | 9x | 243x |
| | Lysophosphatidylcholine | 9x | 243x |

As shown in Table 6, phosphorylcholine-containing lipids produce significant apparent increases in StuI activity which may be due to stabilization of the enzyme by the lipids. Similar results are observed with other restriction endonucleases.

EXAMPLE 5

The Effect of Preincubation on Restriction Digests

Figure 3:
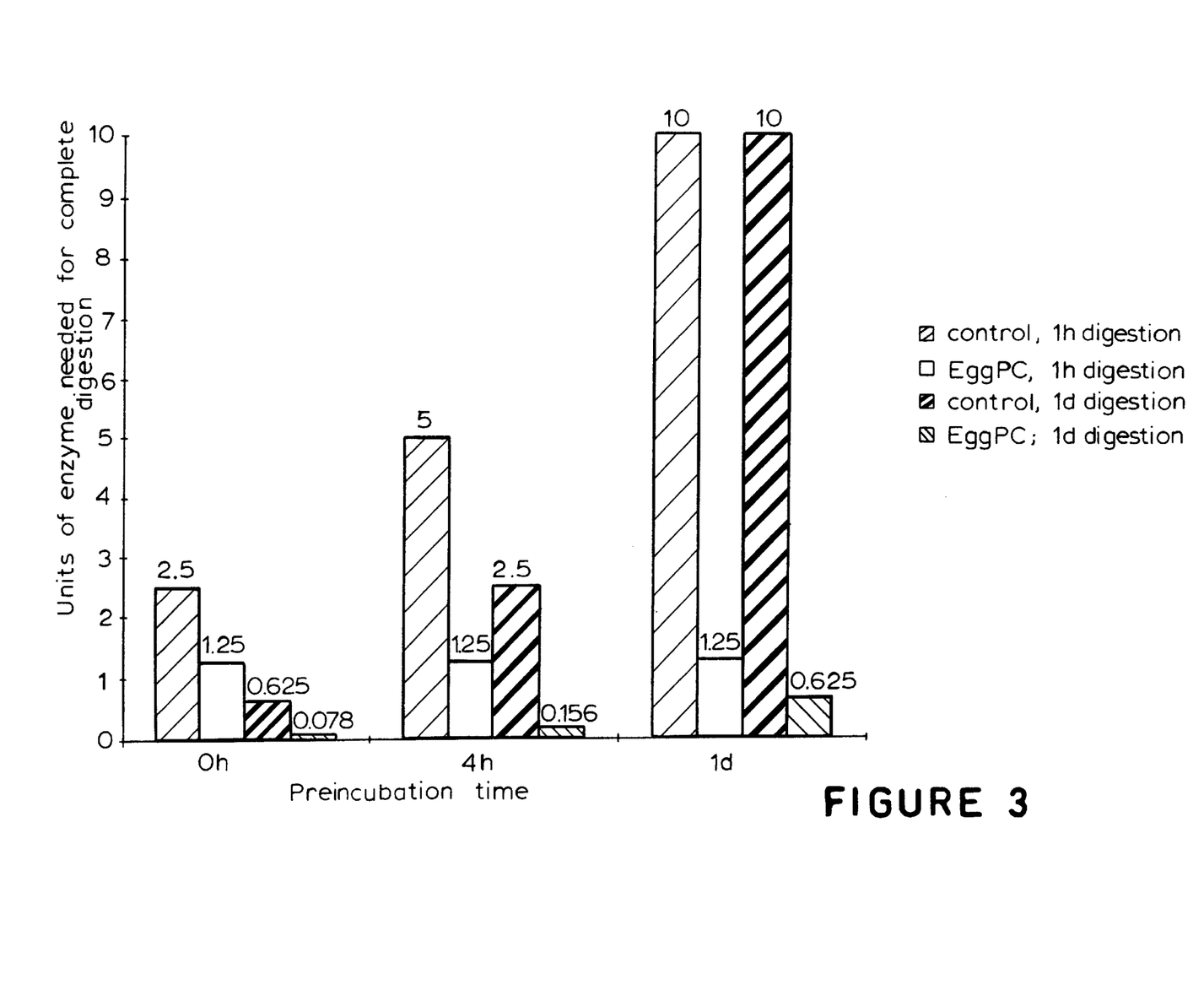
FIG. 3 is a bar graph of the effect of preincubation of StuI with lipids on complete digestion of bacteriophage lambda DNA.

Experiments were conducted to determine the effect of preincubation with lipids on the activation of restriction endonucleases. In one experiment, various concentrations of the endonuclease, StuI, were preincubated in the reaction buffer specified by the manufacturer and in the presence of 20 μM egg yolk phosphatidylcholine. Control samples were incubated in the buffer alone. Preincubation time was either 4 hours or 1 day, at which time 1 μg bacteriophage lambda DNA was added and digestion was allowed to run to completion. For comparison, reactions were run without preincubation. The results are shown in FIG. 3. For each incubation time point in FIG. 3, the first bar represents the control in a one hour digestion, the second bar represents the sample containing phosphatidylcholine in a one hour digestion, the third bar represents the control in a one day digestion, and the fourth bar represents the phosphatidylcholine-containing sample in a one day digestion.

Without preincubation, egg yolk phoshpatidylcholine provides a two-fold apparent increase in StuI activity in a one hour complete digest (i.e., one-half as much enzyme is needed to achieve complete digestion in one hour when lipids are present) and an 8-fold increase in a one day digest. However, after four hours of preincubation, the amount of enzyme necessary for complete digestion in the absence of lipids increases significantly while the amount of enzyme necessary for complete digestion remains the approximately the same as in the case of no preincubation. After one day of preincubation, the results are even more dramatic, showing that the presence of lipids not only increases apparent enzyme activity, but that lipids also provide a stabilizing effect.

Figure 4:
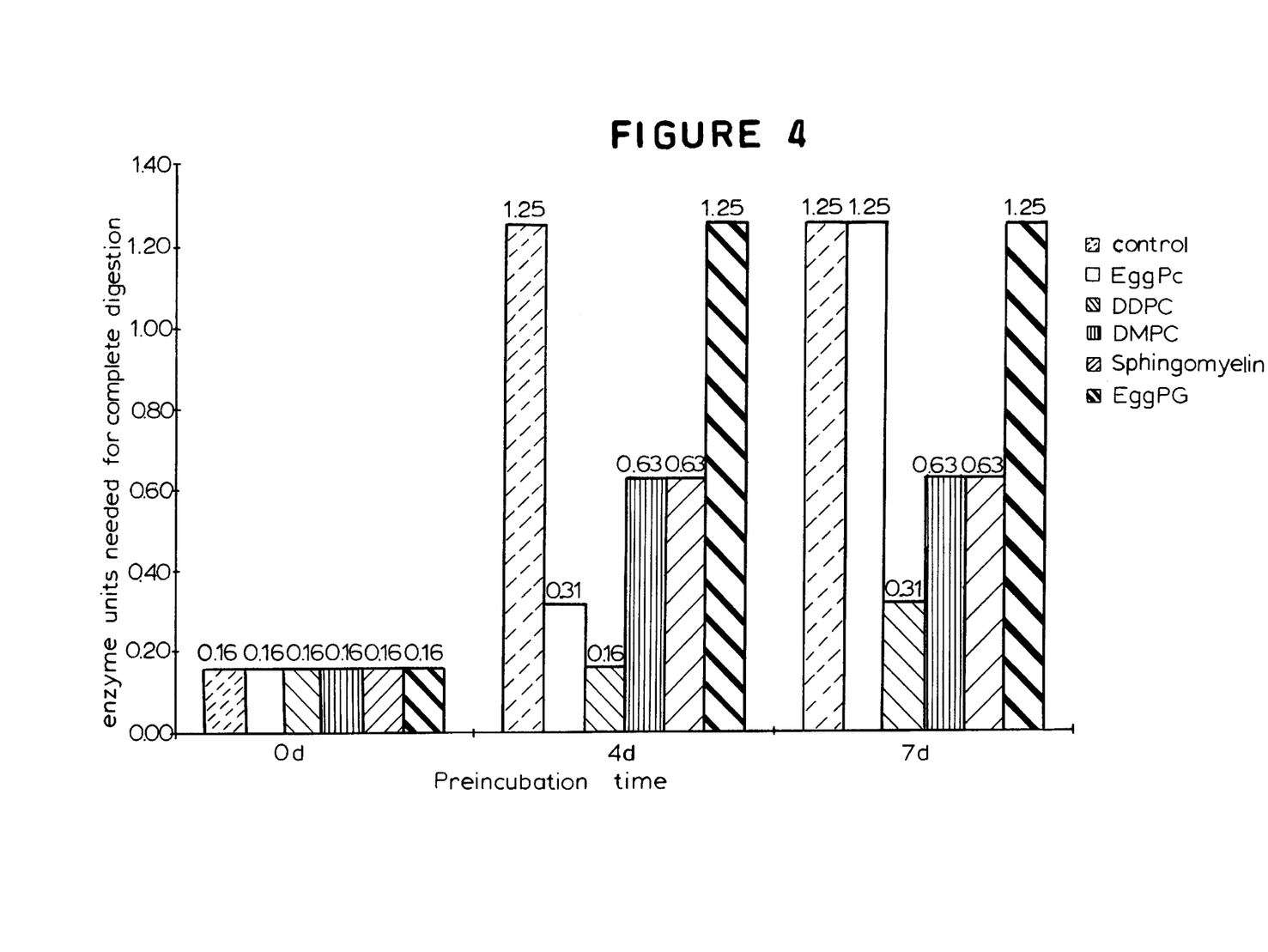
FIG. 4 is a bar graph of the effect of preincubation of EcoRI with lipids on digestion of bacteriophage lambda DNA.

In a second experiment, EcoRI was preincubated with one of several lipids and reaction buffer for either 4 days or 7 days. For comparison, a digestion was run without preincubation. The results are shown in FIG. 4, wherein for each time period (0 days, 4 days, or 7 days), the first bar represent the control (i.e., enzyme in reaction buffer without lipid), the second bar represents results obtained with egg phosphatidylcholine preincubation, the third bar represents results obtained with didecylphosphatidylcholine, the fourth bar represents results obtained with dimyristoylphosphatidylcholine, the fifth bar represents results obtained with sphingomyelin preincubation, and the sixth bar represents results obtained with preincubation with egg phosphatidylglycol.

As shown in the Figure, after four days of incubation, the control (no lipid, bar 1) and the phosphatidylglycol-containing sample required from 2-to-8 times more enzyme for complete digestion in four hours than did phosphorylcholine-containing samples. After 7 days of incubation, didecylphosphatidylcholine, dimyristoylphosphatidylcholine, and sphingomyelin-containing samples all provided enzyme activation. However, the egg phosphatidylcholine-containing sample was equivalent to control levels at that time.

The results reported above show that phosphorylcholine-containing lipids provide stable activation of restriction enzymes even during prolonged storage.

What is claimed is:

1. A method for digesting DNA or RNA with a restriction endonuclease, comprising the step of:
    digesting said DNA or RNA in solution, in a cell-free digestion reaction mixture comprising a lipid having a phosphorylcholine moiety,
    said cell-free digestion reaction mixture further comprising a restriction endonuclease and a suitable reaction buffer,
    said lipid being present in said cell-free digestion reaction mixture at a concentration effective to increase the rate of said digesting of said DNA or RNA by said restriction endonuclease.

2. The method according to claim 1, wherein said lipid is selected from the group consisting of didecyl phosphatidylcholine, egg phosphatidylcholine, 1-palmitoyl-2-acetyl phosphatidylcholine, dimyristoyl phosphatidylcholine, and lysophosphatidylcholine.

3. The method according to claim 1, wherein said lipid is present in said solution in a concentration from about 10 μM to about 50 μM.

4. A method for digesting isolated DNA or RNA, comprising the steps of:
    (a) preparing a mixture comprising:
        (i) isolated DNA or RNA, (ii) a lipid having a phosphorylcholine moiety,
(iii) a restriction endonuclease, and
(iv) a suitable reaction buffer; and (b) incubating said mixture, thereby digesting said isolated DNA or RNA, wherein said lipid is present in said mixture in an amount effective to increase at least one of the rate and yield of a restriction endonuclease digestion, relative to an identical restriction endonuclease digestion of isolated DNA or RNA wherein said mixture is free of said lipid.

5. A method according to claim 4 wherein said lipid is of the formula X—$PO_4^-$—Y, wherein X—$PO_4^-$ is a phosphorylcholine moiety and Y is a hydrophobic moiety.

6. A method according to claim 4 wherein said lipid comprises a phosphatidylcholine.

7. A method according to claim 4 wherein said lipid is selected from the group consisting of didecyl phosphatidylcholine (PC), didecanoyl PC, dimyristoyl PC, dihexadecyl PC, dipalmitoyl PC, dioleoyl PC, sphingomyelin, sphingosyl PC, 1-palmitoyl-2-acetyl PC, 1-palmitoyl-2-octyl PC, lysophosphatidylcholine, and mixtures thereof.

8. A method according to claim 4 wherein said lipid is selected from the group consisting of didecyl phosphatidylcholine (PC) and dimyristoyl PC.

9. A method according to claim 4 wherein said lipid comprises phosphatidylcholine derived from egg yolk.

10. A method according to claim 4 wherein said mixture further comprises stearylamine.

11. A method according to claim 10 wherein the molar ratio of lipid having a phosphorylcholine moiety to stearylamine in said mixture is about 1:1.

12. A method according to claim 4 wherein said lipid is present in said mixture at a concentration from about 2 $\mu$M to about 250 $\mu$M.

13. A method according to claim 4 wherein said lipid is present in said mixture at a concentration from about 10 $\mu$M to about 50 $\mu$M.

14. A method according to claim 4 wherein said restriction endonuclease is selected from the group consisting of StuI, AluI, EcoRV, HaeIII, HindIII, PvuII, RsaI, StuI, PuII, BasII, BglII, EcoRI, HaeII, Sau3AI, and combinations thereof.

15. A method according to claim 12 wherein said restriction endonuclease is selected from the group consisting of PstI, BamHI, and combinations thereof.

16. A method according to claim 4 wherein said restriction endonuclease is TaqI.

17. A composition for buffering an endonuclease reaction between a restriction endonuclease enzyme and isolated DNA, said composition containing magnesium ions ($Mg^{+2}$), dithiothreitol (DTT), a Tris buffer, and sodium ions ($Na^+$) or potassium ions ($K^+$), wherein the improvement comprises a lipid of the formula X—$PO_4^-$—Y in said composition, wherein X—$PO_4^-$ is a phosphorylcholine moiety and Y is a hydrophobic moiety, and wherein said lipid is present in said composition at a concentration from about 2 $\mu$M to about 250 $\mu$M.

18. A composition according to claim 17, wherein said lipid is present in said composition at a concentration from about 10 $\mu$M to about 50 $\mu$M.

19. A composition according to claim 17, wherein said lipid is selected from the group consisting of micelle-forming lipids, liposome-forming lipids, and mixtures thereof.

20. A composition according to claim 17, wherein said lipid comprises a phosphatidylcholine.

21. A composition according to claim 17, wherein said lipid is selected from the group consisting of didecyl phosphatidylcholine (PC), didecanoyl PC, dimyristoyl PC, dihexadecyl PC, dipalmitoyl PC, dioleoyl PC, sphingomyelin, sphingosyl PC, 1-palmitoyl-2-acetyl PC, 1-palmitoyl-2-octyl PC, lysophosphatidylcholine, and mixtures thereof.

22. A composition according to claim 17, wherein said lipid is selected from the group consisting of didecyl phosphatidylcholine (PC) and dimyristoyl PC.

23. A composition according to claim 17, wherein said lipid comprises phosphatidylcholine derived from egg yolk.

24. A composition according to claim 17, wherein said composition further comprises stearylamine.

25. A composition according to claim 24 wherein the molar ratio of lipid of the formula X—$PO_4^-$—Y to stearylamine in said composition is about 1:1.

26. A composition according to claim 17 which is free of restriction endonuclease enzyme.

27. A composition useful as a restriction endonuclease buffer for a cell-free restriction endonuclease reaction, said composition comprising potassium glutamate, magnesium acetate, Tris acetate, mercaptoethanol, and a lipid of the formula X—$PO_4^-$—Y, wherein X—$PO_4^-$ is a phosphorylcholine moiety and Y is a hydrophobic moiety.

28. A composition according to claim 27, wherein said lipid is present in said composition at a concentration from about 2 $\mu$M to about 250 $\mu$M.

29. A composition according to claim 27, wherein said composition further comprises stearylamine.

30. A composition according to claim 29 wherein the molar ratio of lipid of the formula X—$PO_4^-$—Y to stearylamine in said composition is about 1:1.

31. A composition according to claim 27, wherein said lipid is present in said composition at a concentration from 10 $\mu$M to 50 $\mu$M.

32. A composition according to claim 27, wherein said lipid of the formula X—$PO_4^-$—Y comprises a phosphatidylcholine.

33. A composition according to claim 32, wherein said lipid of the formula X—$PO_4^-$—Y is selected from the group consisting of didecyl phosphatidylcholine (PC), didecanoyl PC, dimyristoyl PC, dihexadecyl PC, dipalmitoyl PC, dioleoyl PC, sphingomyelin, sphingosyl PC, 1-palmitoyl-2-acetyl PC, 1-palmitoyl-2-octyl PC, lysophosphatidylcholine, and mixtures thereof.

34. A method for digesting DNA with one or more restriction endonucleases, comprising the step of:
    contacting DNA with one or more restriction endonucleases, wherein said contacting is conducted in a digestion reaction mixture comprising a suitable reaction buffer and a lipid, wherein said lipid consists essentially of lipids having a phosphorylcholine moiety, and wherein said lipid is present in said digestion reaction mixture at a concentration effective to increase the rate of said digesting of said DNA or RNA by said restriction endonuclease, relative to the rate of an identical method for digesting DNA wherein said digestion reaction mixture is essentially free of said lipid.

35. A method according to claim 34 wherein said lipid is present in said reaction mixture at a concentration of 10 $\mu$M–50 $\mu$M.

* * * * *